United States Patent [19]
Werblin et al.

[11] Patent Number: 5,123,921
[45] Date of Patent: Jun. 23, 1992

[54] SYNTHETIC INTRACORNEAL LINES AND METHOD OF MANUFACTURE

[75] Inventors: Theodore P. Werblin, Bluefield, W. Va.; Anilbhai S. Patel, Seattle, Wash.

[73] Assignee: Nestle S.A., Vevey, Switzerland

[21] Appl. No.: 677,595

[22] Filed: Mar. 27, 1991

Related U.S. Application Data

[63] Continuation of Ser. No. 96,971, Sep. 14, 1987, abandoned.

[51] Int. Cl.$^5$ ............................................. A61F 2/14
[52] U.S. Cl. ............................................. 623/5; 623/4
[58] Field of Search .................................. 623/4–5

[56] References Cited

U.S. PATENT DOCUMENTS

| | | | |
|---|---|---|---|
| 4,512,039 | 4/1985 | Lieberman | 623/6 |
| 4,607,617 | 8/1986 | Choyce | 623/5 |
| 4,676,790 | 6/1987 | Kern | 623/5 |
| 4,715,858 | 12/1987 | Lindstrom | 623/5 |
| 4,810,082 | 3/1989 | Abel | 623/5 |
| 4,865,601 | 9/1989 | Caldwell | 623/5 |

OTHER PUBLICATIONS

Sendele et al., Intracorneal Lens Implantation, Arch. Ophthalmol. 101: 940–944, 1983.
Werblin et al., Myopic Hydrogel Keratophakia: Preliminary Report, Cornea 3: 197–204, 1985.
Werblin, et al., "Myopic Correction Using Alloplastic Implants in Non-Human Pirmates—A Preliminary Report," *Annals of Ophthalmology*, pp. 1127–1130 (Dec., 1984).
Werblin, et al., "Myopic Hydrogel Keratophakia," *Cornea*, 6(3):197–201 (1987).
Werblin, et al., "Hydrogel Keratophakia–Improvements in Myopic Lens Design," *ARVO Abstracts*, 9–10:30 (Apr. 28, 1986).

*Primary Examiner*—Randall L. Green
*Assistant Examiner*—D. Willse
*Attorney, Agent, or Firm*—Barry L. Copeland; Jeffrey S. Schira

[57] ABSTRACT

A lens for implantation into the cornea of the eye for providing correction for myopia and myopia with accompanying astigmatism wherein a corneal cap section is removed and an implant bed is created to receive the intracorneal lens. The intracorneal lens is formed of a hydrogel type material or other material highly compatible with corneal physiology. In the range of lens powers of approximately −1.0 diopters to −30.0 diopters, the posterior radius of curvature conforms to the receiving surface of the lamellar bed of the cornea and the anterior surface has the radius of curvature necessary to provide the desired lens power for achieving the desired change in the refractive power of the cornea. The lens includes a peripheral transitional zone to join the anterior surface and posterior surface to allow the lens to be implanted onto the corneal bed and to allow for a smooth overlay of the replaced corneal cap section.

29 Claims, 3 Drawing Sheets

SYNTHETIC INTRACORNEAL LINES AND METHOD OF MANUFACTURE

This application is a continuation of application Ser. No. 07/096,971, filed Sep. 14, 1987, now abandoned.

FIELD OF THE INVENTION

The field of this invention relates to prosthetic lenses designed to be implanted in the cornea thereby modifying the corneal curvature and thus altering the corneal refractive power for correction of conditions of myopia and myopia with accompanying astigmatism.

BACKGROUND OF THE INVENTION

Research into the utilization of corneal grafts and implants to affect corneal curvature began with the work of Dr. Jose Barraquer of Bogota, Columbia and others prior to 1950. Dr. Barraquer's research involved the use of implanted donor corneal lenticules that had been removed from a donor eye with a microkeratome, frozen, lathed and placed within the recipient cornea to achieve a steepening of the anterior corneal curvature. Within the last two decades, research has been done in determining compatible implant materials which may be successful as synthetic corneal implants for the correction of hyperopia. A number of researchers have determined that a highly compatible and desirable implant may be made from a hydrogel material. See inter alia, Werblin, et al., "Stability of Hydrogel Intracorneal Implants in Non-Human Primates," CLAO Journal 9:157–161 (1983). Binder, et al., "Hydrogel Keratophakia in Non-human Primates," Current Eye Research, 1:535–42 (1981); Koenig, et al., "Refractive Keratoplasty With Hydrogel Implants in Primates," Ophthalmic Surgery, 15:225–229 (1984). It has been recognized that the objective of such hydrogel implants is to alter the anterior corneal curvature to hopefully provide a predictable, stable and reversible change in refraction. Because of the large difference in the refractive indices between the precorneal tear film and air, small changes in the corneal radius will result in relatively large changes in refractive power. Hydrogel materials have been found to be sufficiently permeable to water and metabolic nutrients to maintain normal corneal physiology. For the most part to date, however, that work has been carried out in order to provide steepening for hyperopic correction.

It has been determined that the more desirable surgical technique for the implantation of a hydrogel lens is the surgical procedure which utilizes the Barraquer microkeratome for lamellar keratectomy. Beekhuis, McCarey, et al. "Hydrogel Keratophakia: A Microkeratome Dissection in the Monkey Model," British Journal of Ophthalmology, 70:192–198 (1986); McCarey, et al., "Hydrogel Keratophakia: A Freehand Pocket Dissection in the Monkey Model," British Journal of Ophthalmology," 70:187–191 (1986); Sendele, et al. "Intracorneal Lens Implantation," Arch Ophthalmology, 101:940–944 (1983). It has been suggested that the main reason for use of microkeratome as compared to a pocket dissection is the necessity of severing the anterior collagen bundles and Bowman's layer in order to allow these structures to assume the anterior corneal curvature change imposed as a result of the implant. Binder, et al, "Hydrophilic Lenses for Refractive Kerotoplasty: The Use of Factory Lathed Materials," CLAO Journal 10:105–111 (1984); McCarey, et al., "Hydrogel Keratophakia: A Freehand Pocket Dissection in the Monkey Model," British Journal of Ophthalmology," 70:187–191 (1986).

Over these three and one-half decades of research, virtually all of the work has related to correction of hyperopia. In the correction of hyperopia, the purpose of the implant is to steepen the corneal curvature. There has been much less research activity with the even more complex problem of utilizing corneal implants to correct myopia. Werblin, et al., "Myopic and Hyperopic Hydrogel Keratophakia," Arch. Soc. Oftal. Optom., 18:131-143 (1984); Werblin, et al., "Myopic Hydrogel Keratophakia: Preliminary Report," Cornea, 3:197-204 (1985); Werblin, et al., "Myopic Correction Using Alloplastic Implants in Non-Human Primates—A Preliminary Report," Annals of Ophthalmology, 1127-1130 (1984). This is in part because the corneal curvature must not be steepened as in the correction of hyperopia but rather the corneal curvature must be flattened for the correction of myopia. It has been concluded that negative refractive lenses can be implanted into the cornea of primates in order to produce a substantial corneal flattening. While the initial flattening produced by research was irregular, it has been suggested that enlarging the size of the lenticule and the optical zone could possibly produce a corneal flattening which would become more regular. For primates, positive results were obtained utilizing lenses having a diameter of 6.75 mm as compared to prior results utilizing implants at 5.5 mm. Werblin, Patel, "Hydrogel Keratophakia: Improvements in Myopic Lens Design," ARVO Abstracts 1986:14.

While prior research has pointed the way toward the most desirable surgical procedure using the microkeratome and at least one school of researchers has concluded that hydrogel materials are prime candidates to be utilized as corneal implants, little work has been done to actually design a corneal implant lens having negative refractive power in order to correct myopia in humans. Some work has been done in an effort to predict the ultimate corneal refractive alteration caused by hydrogel keratophakia. In the paper entitled "Predicting Refractive Alterations With Hydrogel Keratophakia," authors Watsky, McCarey and Beekhuis presented algorithms that utilized elementary optics to calculate the total corneal power produced through intracorneal lens implantation via either pocket or microkeratome dissection. Investigative Ophthalmology and Visual Science, 26:240-243 (1985). In the paper "Alloplastic Refractive Keratophalia: A Comparison of Predictive Algorithms," the authors Watsky and McCarey compared the accuracy of three different algorithms to predict actual in vivo power of a lens: (1) a back vertex power algorithm ("sandwich" algorithm); (2) paraxial ray tracing and (3) meridional ray tracing for implanted positive hydrogel and polysulfone implants. See also, Churms, "The Theory and Computation of Optical Modifications to the Cornea and Refractive Keratoplasty," American Journal of Optometry and Physiological Optics, 56(2):67 (1979). See also, Mester, et al., "Measurement and Calculation of Refraction in Experimental Keratophakia With Hydrophilic Lenses," Opthal. Res. 8:111-116 (1976); Arffa, et al., "Keratometry in Epikeratophakia," Journal of Refractive Surgery 2:61-64 (1986).

U.S. Pat. No. 4,607,617 of Choyce entitled "Apparatus and Method of Improving Eyesight," discloses a corneal implant made of a polysulfone plastics material designed to be implanted between layers of the cornea to correct eyesight defects. The nature of the polysulfone material disclosed in the '617 patent is quite different from the hydrogel materials previously discussed in that the polysulfone material has a high refractive index relative to that of the cornea. Further, it is believed that the hydrophilic, water permeable nature of the hydrogel allows more flexibility in placement of an implant as compared to the implanting of polysulfone that is not water impermeable. U.S. Pat. No. 4,612,012 of White is directed to a prosthesis which supposedly provides for the surgical replacement of all or a portion of the cornea, the implant having a peripheral portion having an outer tissue contacting surface of a biologically compatible material. U.S. Pat. No. 4,298,004 of Schachar, et al., discloses a surgical material wherein collagen or other suitable material is injected into an incision in the cornea in order to alter the radius of curvature.

SUMMARY OF THE INVENTION

A lens is designed for implantation in the cornea of an eye for the correction of myopia or myopia with accompanying astigmatism. The intracorneal lens of this invention is adapted to be placed onto a receiving lamellar surface of an intracorneal bed formed by surgical procedure. The surgical procedure, utilizing an instrument known as a microkeratome, includes the temporary removal of a corneal section or cap and immediate re-positioning thereof with sutures, implantation of the intracorneal lens onto the corneal bed and full reattachment of the corneal section.

The intracorneal lens of this invention is a one-piece member having an anterior surface, a posterior surface and a peripheral transition zone which serves to join the anterior and posterior surfaces. The overall configuration of the lens is circular as viewed from the central axis of the lens. The anterior surface of the intracorneal lens is convex and the posterior surface is concave. The peripheral transition zone of the lens includes an annular surface which cooperates to Join the anterior and posterior surfaces in order to allow the lens to be implanted onto the corneal bed and to allow for a smooth overlay of the replaced corneal section. The intracorneal lens of this invention is designed in a series of steps uniquely adapted to provide a resultant lens for the corneal environment. This description is intended as summary only. The invention will be fully described in the Description of the Preferred Embodiment and the claims will set forth the invention for which patent protection has been sought.

DESCRIPTION OF THE PREFERRED EMBODIMENT

Although research into intracorneal lens implants has been ongoing for over three decades, no one has perfected an intracorneal lens implant which may be successfully implanted to correct myopia or myopia with accompanying astigmatism. This invention is directed to the manufacture of an intracorneal lens or lenticule identified in the drawings by the letter "I" which is specifically designed for the correction of myopic conditions, with and without accompanying astigmatism. Throughout this disclosure, the power of the lens I has been referred to; however, it should be understood that the power of the lens I as used here refers to the change in refractive power of the cornea which will result from the change in curvature of the anterior surface of the cornea. This nomenclature is used, however, since this is the nomenclature used by physicians and will be best understood by those persons.

The intracorneal lens I of this invention is made of a material which is compatible with the tissue of the cornea thereby allowing the cornea physiology to remain functional without deterioration for prolonged periods after implantation. The intracorneal lens implant I of the preferred embodiment of this invention is made of a hydrogel material such as the hydrophilic lens manufactured under the trademark Permalens by CooperVision, Inc. of Palo Alto, Calif. Such hydrogel material is known to have a water content, when wetted, of at least 70%. The material is identified as Perfilcon-A material in the nomenclature of the United States Adopted Name Council. Such hydrogel material as used in the intracorneal lens I of this invention has a refractive index of $1.380+/-0.010$, which is similar to the adjusted corneal refractive index of the human eye, which is 1.3375. See, Sanders, Hoffmann, Salz, "Refractive Corneal Surgery," Slack, Inc., 1986. It has been determined that such hydrogel material with its hydrophilic characteristics has sufficient porosity to transmit through osmosis water and metabolic flux ($CO_2$, glucose, $O_2$, etc.) that are deemed necessary to moisten and nourish tissue throughout the cornea. Such hydrogel materials have been found to be biocompatible with corneal tissue and can be replaced without damage to surrounding corneal tissue. The hydrogel can be formed as described or be coated, combined or copolymerized with an appropriate additive to make the lens capable of absorbing UV radiation.

Figure 2:
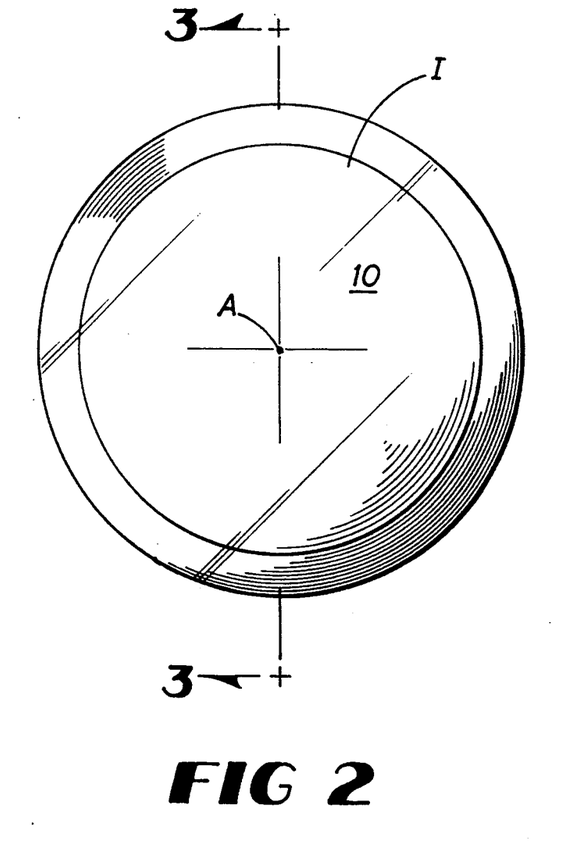
FIG. 2 is a front view of the intracorneal lens of this invention.
Figure 3:
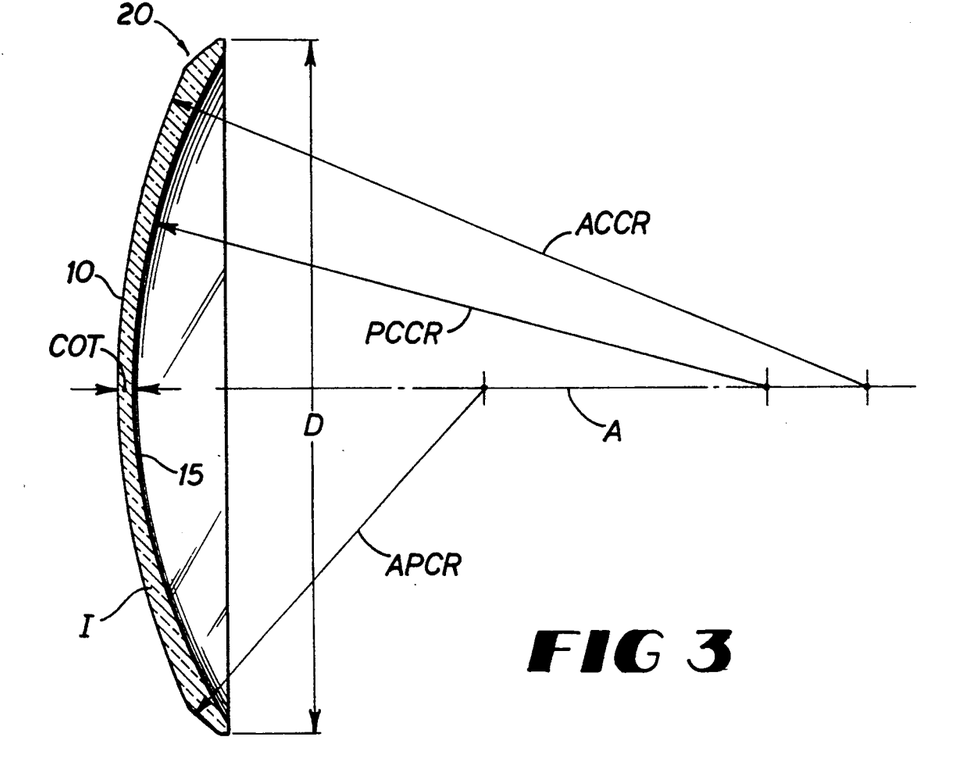
FIG. 3 is a transverse sectional view taken along line 3—3 of FIG. 2.
Figure 4:
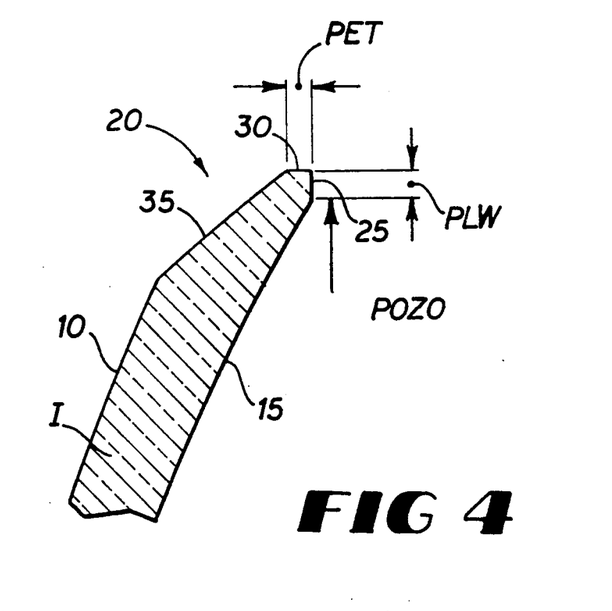
FIG. 4 is an enlarged view of the peripheral transition zone for the intracorneal lens of this invention.

Referring to FIGS. 2–4, the intracorneal lens I or lenticule of this invention is formed of an anterior surface 10 which is spherical in the correction of myopia. The anterior surface 10 is convex as illustrated in the cross-sectional view of FIG. 3, which is taken along sectional line 3—3 of FIG. 2. Anterior surface 10 has a radius of curvature identified as ACCR (Anterior Central Curve Radius). The intracorneal lens I further includes a spherical posterior surface 15 which is concave as viewed in the cross-sectional view of FIG. 3. The radius of curvature of the posterior surface 15 is identified as PCCR (Posterior Central Curve Radius). Referring to FIG. 3, the anterior surface 10 and posterior surface 15 are joined at the periphery of the lens 10 by three surfaces which combine to form the peripheral transition zone 20. The peripheral transition zone 20 is formed of a first annular surface 25, a second annular surface 30 and a third annular surface 35 which cooperate to Join the anterior surface 10 and posterior surface 15 of the lens.

While the posterior and anterior surfaces 10 and 15 are disclosed in FIGS. 2-4 as being spherical, it should be understood that under certain conditions, such as the mismatch conditions described later, that either or both the posterior and anterior surfaces of the lens I may be aspherical when conformed to the receiving surface S3 of the lamellar bed LB.

The first annular surface 25 is in a plane perpendicular to the central axis A of the lens. The central axis A is theoretically coterminous with the visual axis of the fovea, which is the central pit in the macula that produces sharpest vision, containing a high concentration of cones and no retinal blood vessels. Referring to FIG. 3, the first annular surface 25 has a center point on the axis A and an internal edge diameter POZD (Posterior Optic Zone Diameter). The radial width of the first annular surface 25 is identified in FIG. 3 as PLW (Posterior Land Width).

The second annular surface 30 is also generated about a point along the axis A. The annular surface 30 is perpendicular to the annular surface 25 and is in a plane parallel to the line of axis A. The width of the second annular surface 30 is defined as PET (Peripheral Edge Thickness).

The third annular surface 35 is an annular spherical segment which serves to join the second annular surface 30 and the anterior surface 10 together. The third annular surface 35 is generally spherical in the cross-sections of FIGS. 3 and 4, having a radius of curvature identified as APCR (Anterior Peripheral Curve Radius).

The cross-sectional contour of the peripheral transitional zone 20 as viewed in FIGS. 3 and 4 is an important configuration for the intracorneal lens I to function as intended. The transitional zone 20 must serve a number of purposes in vivo. Anterior surfaces including anterior surface 10 and third annular surface 35 must be positioned with respect to posterior surface 15 and first and second peripheral annular surfaces 25 and 30 to allow the corneal section, if removed by the surgical procedure of lamellar keratectomy, to fit smoothly against the outer corneal surface upon replacement. Additionally, the transitional zone configuration 20 must properly adjoin surrounding tissue in the lamellar bed of the cornea to cause the lens I to remain in a stable position and to prevent any agitation which might encourage undesirable cell growth around the edges of the implant I. The particular combination and configuration of surfaces 25, 30 and 35 cooperate to meet these goals.

Figure 5:
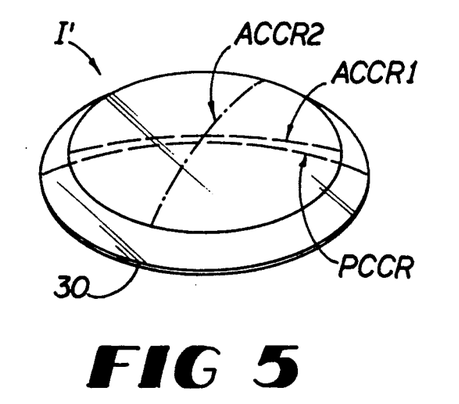
FIG. 5 is a view of an intracorneal lens of this invention for the correction of myopia with accompanying astigmatism by the anterior surface of the lens.

Referring to FIG. 5, the intracorneal lens I' of this invention is provided for the correction of myopia with accompanying astigmatism. The refractive power of a astigmatic cornea is not uniform in all meridians. Therefore, the implant I' is designed to be toric in at least its anterior surface in order to provide the necessary corneal correction for myopia with accompanying astigmatism. In FIG. 5, the term ACCR1 refers to the radius of curvature of the lens I' in a cross-section taken through the dotted line ACCR1. The term ACCR2 refers to a radius of curvature for the anterior surface taken through a cross-section of ACCR2. For correction of myopia with astigmatism, ACCR1 will be unequal to ACCR2.

Figure 5A:
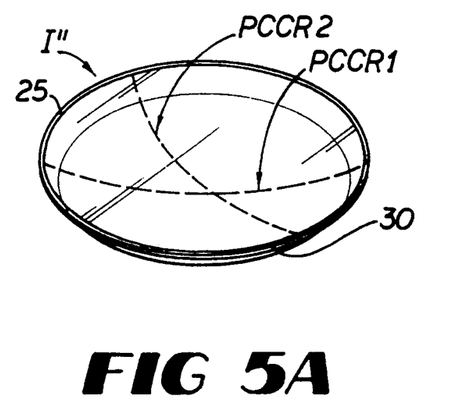
FIG. 5A is a view of an intracorneal lens of another embodiment of the invention for the correction of myopia with accompanying astigmatism by the posterior surface of the lens.

Referring to FIG. 5A, the intracorneal lens I" of this invention is provided as another embodiment for the correction of myopia with accompanying astigmatism. The implant I" is designed to be toric in at least its posterior surface in order to provide the necessary corneal correction for myopia with accompanying astigmatism. In FIG. 5A, the term PCCR1 refers to the radius of curvature of the lens I" in a cross-section taken through the dotted line PCCR1. The term PCCR2 refers to a radius of curvature for the posterior surface taken through a cross-section of PCCR2. For correction of myopia with astigmatism, PCCR1 will be unequal to PCCR2.

Figure 1:
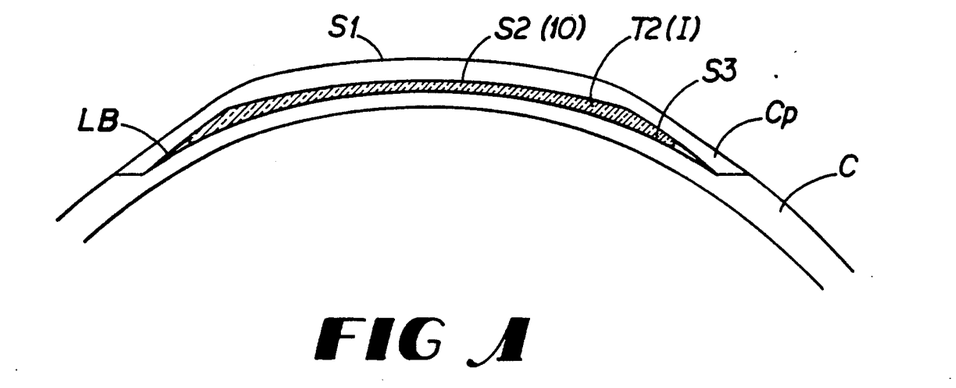
FIG. 1 is a schematic view of the position of an intracorneal implant of this invention after implantation in the eye.

Referring now to FIG. 1, a schematic of the cornea C of the eye is illustrated. In FIG. 1, the designation Cp identifies the corneal cap which is removed using the lamellar keratectomy surgical procedure, which uses an instrument known as a microkeratome. Utilizing the oscillating blade of the microkeratome (not shown), the corneal cap Cp is removed to a depth of in the range of 0.2-0.4 mm, and preferably 0.3 mm, exposing the underlying stroma of receiving surface S3 of the cornea. The surgical procedure of the lamellar keratectomy leaves an annular recess or surgical pocket defined as the lamellar bed LB. The lamellar bed LB includes the lamellar implant receiving surface S3.

The actual dimensions of the intracorneal lens I of FIGS. 2-4 are critical to the successful implantation of the lens. For a range of lens power of approximately −1.0 to −30.0 diopters, the posterior surface 15 is designed to have a radius of curvature which conforms to the receiving surface S3 of the cornea. The radius of curvature of the posterior surface 15 corresponds to the radius of curvature of the anterior surface of the cornea for corneal powers in the range of 38-51 diopters minus the lamellar section thickness. For each such posterior surface curvature, the anterior surface 10 will be provided with the radius of curvature ACCR necessary to provide the desired lens power for achieving the desired change in the refractive power of the cornea. As previously discussed, "lens power" as referred to for the implant I is actually the resultant change in power of the cornea after implant as measured by a keratometer. Whereever "diopters" are referred to, the term is used to indicate refractive power measured by a keratometer in diopters. For example, if the corneal power is determined to be 40.0 diopters, the lens I will be designed to provide the posterior surface 15 curvature which will conform to the receiving surface S3 of FIG. 1. The anterior surface 10 will have a radius of curvature ACCR necessary to provide the desired lens for achieving the desired change in refractive power of the cornea. For corneal powers in the range of 38-51 diopters, the radius of curvature S3 and thus PCCR will be as follows in Table 1, for a depth of corneal section of 0.3 mm:

TABLE 1

| Corneal Diopter | Corneal Radius of Curvature (mm) | PCCR (.3 mm Section) mm |
| --- | --- | --- |
| 38.0 | 8.882 | 8.582 |
| 39.0 | 8.654 | 8.354 |
| 40.0 | 8.438 | 8.138 |
| 41.0 | 8.232 | 7.932 |
| 42.0 | 8.036 | 7.736 |
| 43.0 | 7.849 | 7.549 |

TABLE 1-continued

| Corneal Diopter | Corneal Radius of Curvature (mm) | PCCR (.3 mm Section) mm |
| --- | --- | --- |
| 44.0 | 7.670 | 7.370 |
| 45.0 | 7.500 | 7.200 |
| 46.0 | 7.337 | 7.037 |
| 47.0 | 7.181 | 6.881 |
| 48.0 | 7.031 | 6.731 |
| 49.0 | 6.888 | 6.588 |
| 50.0 | 6.750 | 6.450 |
| 51.0 | 6.618 | 6.318 |

In determining the critical dimensions of the intracorneal lens I in a preferred embodiment of the invention, it has been determined that the radius of curvature PCCR of the posterior surface 15 of the lens can be constant for all receiving surfaces S3 corresponding to corneal powers in the range of 38–51 diopters and with a corneal thickness of the corneal cap Cp within the range of 0.2–0.4 mm and assure predictable refraction throughout the optic zone with desirable accuracy.

It has been determined that the intracorneal lens I of this invention should be manufactured utilizing a posterior surface radius of curvature of 7.549 mm. This dimension was determined from a study of the average refractive powers of corneas and an interpolation of that study which determined that the average receiving surface S3 of the lamellar bed LB would have a radius of curvature corresponding to the radius of curvature of a corneal power of 43 diopters minus a 0.3 mm lamellar section. It was determined that this base curve of 7.549 mm could provide a sufficient match to patients having an actual corneal power with the range of 38–51 diopters, minus a thickness of the corneal cap Cp in the range of 0.2–0.4 mm, and preferably 0.3 mm, to assure predictable refraction throughout the optic zone with sufficient accuracy.

Referring to FIG. 1, the designation S3 also represents the posterior surface 15 of the lens 10. The designation S2 represents the anterior surface 10 of the lens. The designation S1 represents the anterior surface of the corneal cap Cp. Finally, the designation T2 represents the intracorneal lens I not only in the following formulas but also in FIG. 1.

The power $P_{ICL}$ of the intracorneal lens, identified as "ICL" in the following formulas, is defined as the difference between the expected post-operative corneal power, $P_{C2}$, and the preoperative corneal power, $P_{C1}$.

$$P_{ICL} = P_{C2} - P_{C1} \quad (1)$$

The operative corneal power was modeled by separating the power due to the preoperative anterior surface of the cornea, $P_{SO}$, from other terms, OT.

$$P_{C1} = P_{SO} + OT \quad (2)$$

The preoperative reading for the anterior surface of the cornea determine $P_{SO}$.

$$P_{SO} = \frac{n_C - n_{AIR}}{R_{C1}} \quad (3)$$

where
$n_C = 1.376$, index of cornea tissue,
$n_{AIR} = 1.0003$, index of air, and
$R_{C1} = 37.5/K$, cornea radius of curvature.

K = corneal power in diopters

The vergence of the corneal section removed in the microkeratome procedure and replaced after the implantation is expected to change due to bending. Calculations show that the vergence of this thickness element changes by less than 0.01 diopter throughout the ranges of ICL powers and initial corneal power anticipated.

The postoperative corneal power was modeled by summing the powers due to the several postoperative surfaces and the ICL thickness vergence, as shown in FIG. 1.

$$P_{C2} = P_{S1} + P_{S2} + P_{T2} + P_{S3} + OT \quad (4)$$

Substituting for $P_{C2}$ and $P_{C1}$ in the formula (1), the following resultant equation is attained:

$$\begin{aligned} P_{ICL} &= (P_{S1} + P_{S2} + P_{T2} + P_{S3} + OT) - (P_{S0} + OT) \\ &= P_{S1} + P_{S2} + P_{T2} + P_{S3} - P_{S0} \end{aligned} \quad (5)$$

The receiving surface S3 of the lamellar bed, LB, is assumed to have a radius of curvature, ROC, equal to that of the pre-operative cornea minus the thickness of the corneal section, $t_{cs}$, removed by the microkeratome procedure. The power of the posterior ICL surface is as follows:

$$\begin{aligned} P_{S3} &= \frac{n_H - n_C}{R_{C1} - t_{cs}} \\ &= \frac{n_H - n_C}{(337.5/K) - t_{cs}} \end{aligned} \quad (6)$$

where
$n_H = 1.381$, index of the ICL material.
The ICL thickness vergence is:

$$P_{T2} = \frac{(n_H - n_C)^2 \, t_{ICL}}{n_H R_{AL} (R_{C1} - t_{cs})} \quad (7)$$

where
$t_{ICL}$ = central thickness of the ICL, and
$R_{AL}$ = ICL anterior ROC.
The refraction at the anterior ICL surface is:

$$P_{S2} = \frac{n_H - n_C}{R_{AL}} \quad (8)$$

The ROC of the modified cornea $R_{C2}$ is assumed to be:

$$R_{C2} = R_{AL} + t_{cs}$$

The power of the anterior surface of the modified cornea is:

$$P_{S1} = \frac{n_C - n_{AIR}}{R_{AL} + t_{cs}} \quad (9)$$

The power of the ICL as defined by equation (1) can now be computed by using equations (3), (6), (7), (8), and (9) and computing thereby the various components of equation (5).

Dimensions of an ICL with refractive correction in the range of −1.0 to −30.0 diopters have been determined using the above calculation and are given in the following table, understanding that the actual refractive correction obtained may vary somewhat depending on a number of clinical factors.

TABLE 2

ICL DIMENSIONAL SUMMARY (HYDRATED) FOR AN AVERAGE KERATOMETER OF 43 DIOPTERS

| ICL POWER (DIOPTER) | D | AOZD | ACCR | APCR | POZD | PCCR | TZT | COT | PET | PLW |
|---|---|---|---|---|---|---|---|---|---|---|
| −1.0 | 6.750 | 5.608 | (7.766) | (7.015) | (6.608) | (7.549) | (0.108) | 0.100 | (0.057) | (0.071) |
| −5.0 | 6.750 | 5.608 | (8.512) | (6.195) | (6.608) | (7.549) | (0.153) | 0.100 | (0.057) | (0.071) |
| −10.0 | 6.750 | 5.608 | (8.512) | (6.195) | (6.608) | (7.549) | (0.153) | 0.100 | (0.057) | (0.071) |
| −15.0 | 6.750 | 5.608 | (11.162) | (5.030) | (6.608) | (7.549) | (0.263) | 0.100 | (0.057) | (0.071) |
| −20.0 | 6.750 | 5.608 | (13.191) | (4.691) | (6.608) | (7.549) | (0.315) | 0.100 | (0.057) | (0.071) |
| −25.0 | 6.750 | 5.608 | (16.094) | (4.438) | (6.608) | (7.549) | (0.367) | 0.100 | (0.057) | (0.071) |
| −30.0 | 6.750 | 5.608 | (20.589) | (4.245) | (6.608) | (7.549) | (0.418) | 0.100 | (0.057) | (0.071) |

ABBREVIATION SUMMARY
D - Diameter
AOZD - Anterior Optic Zone Diameter
ACCR - Anterior Central Curve Radius
APCR - Anterior Peripheral Curve Radius
POZD - Posterior Optic Zone Diameter
PCCR - Posterior Central Curve Radius
TZT - Transition Zone Thickness
COT - Central Optic Thickness
PET - Peripheral Edge Thickness
PLW - Posterior Land Width
MM - All Dimensions in Millimeters Referring to the dimensions shown in Table 2, it is firstly noted that the PCCR radius is constant at 7.549 mm, which corresponds to the radius of curvature of an average cornea with a refractive power of 43 diopters minus a lamellar section of 0.3 mm at the receiving surface S3 of the lamellar bed LB. Other constants include the thickness PLW of the first annular surface 25, which is approximately 0.071 mm within the range of the intracorneal lens (ICL) powers in Table 1. Further, the peripheral edge thickness PET of the second annular surface 30 is constant at approximately 0.057 millimeters. The central optic thickness COT is constant at 0.100 millimeters. The outside diameter D of the lens I is 6.75 millimeters. However, it is within the scope of this invention to vary the outside diameter D of the lens I within the range of 5.0 to 8.0 mm with the preferred embodiment being approximately 6.75 mm. The radius of curvature of the anterior central curved surface (ACCR) varies from 7.766 mm (−1.0 diopter power ICL) to 20.589 mm (−30. ICL diopter power). The distance COT between anterior surface 10 and posterior surface 15 as the area A is in the range of approximately 0.05–0.20 mm and preferably approximately 0.10 mm. The radial width of the third annular surface 35 is constant in the embodiment of FIGS. 2-4 but in another embodiment can vary according to the curvature of anterior surface 10 and thickness PET. Table 2 is intended to provide a technical overview of the intracorneal lens I of this invention. It is understood that dimensions for intermediate powers will fall within the parameters set forth in the Table.

One of the hypotheses of the intracorneal lens I design of FIGS. 2-4 of a preferred embodiment of the invention is that the posterior central curved radius PCCR can be held constant at 7.549 mm over the range of corneal power of 38-51 diopters with corneal power correction of −1.0 to −30.0 diopters. It is known from prior experimentation that a lens formed of a hydrogel material is subject to certain adjustments upon implantation. One major adjustment is the conformity of the hydrogel lens to the actual curvature of the receiving surface S3 of the lamellar bed LB. It is one of the important conclusions of a preferred embodiment of this invention that the constant radius of curvature 7.549 mm may be taken for the posterior surface curvature of the lens. The following test proves the validity of this invention.

Test for Geometric Ray Trace Model

Figure 6:
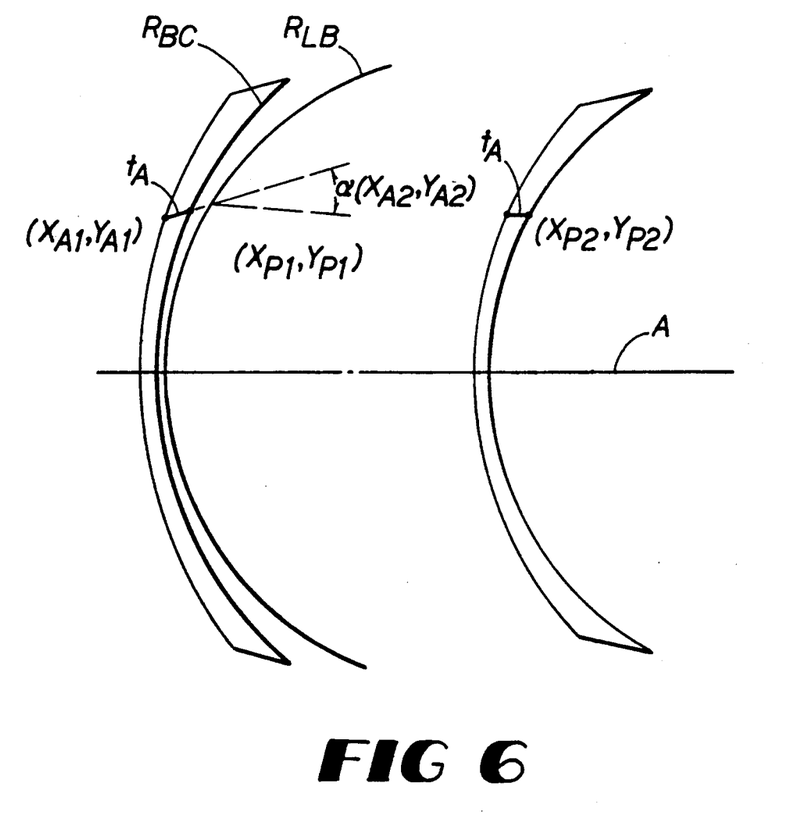
FIG. 6 is a schematic diagram of an algorithm developed to predict the change in refractive power of the cornea due to the lens implant under conditions of mismatch between the posterior surface of the lens and the receiving surface of the lamellar bed.

Since the intracorneal lens I of this invention is formed of a hydrogel material which will bend to conform to the actual surface of the lamellar bed, an initial inquiry is the efficacy of this lens under bending caused by this mismatch. The effect on ICL power of a mismatch between ICL base curve and the radius of curvature (ROC) of the cornea lamellar bed (referred to as S3, supra) has been modeled to test the efficacy of the application of intracorneal lens I of this invention to patients having receiving surface refractive indexes which vary from the 43.0 average. The Geometric Ray Trace Model applied here does not assume that the anterior surface of the conformed intracorneal lens is spherical. See, Watsky, McCarey "Alloplastic Refractive Keratophakia: A Comparison of Predictive Algorithms," CLAO Journal, 12:112-117 (1986). The coordinates of the anterior surface are found by adding the intraocular lens thickness to the coordinates of the posterior surface. Then, a geometric ray tracing program determines the best sphere and the deviation from sphericity across the optical zone. Additionally, the thickness of the conformed intraocular lens was not assumed to be the same as the unconformed, or relaxed, state of the lens except at the center. Reference is made to FIG. 6 in the following formulas: where:

$X_{A1}$, $Y_{A1}$—coordinates of the relaxed ICL anterior surface $X_{A2}$, $Y_{A2}$—coordinates of the conformed ICL anterior surface $X_{P1}$, $Y_{P1}$—coordinates of the related ICL posterior surface $X_{P2}$, $Y_{P2}$—coordinates of the conformed ICL posterior surface $t_A$—ICL thickness parallel to optic axis in conformed state $R_{BC}$—base curve radius of curvature, 43K $R_{LB}$—lamellar bed radius of curvature, varied from 38 to 51K $\alpha$—deflection angle of $t_A$ from conformed (in vivo on corneal bed receiving surface S3) to relaxed state (hydrated at 43 diopters)

The posterior ICL surface or base curve (BC), is mapped onto the lamellar bed (LB).

$$Y_{P2} = R_{LB}\sin\left(\frac{R_{BC}}{R_{LB}} \arcsin\left(\frac{Y_{P1}}{R_{BC}}\right)\right) \quad (1)$$

and $$X_{P2} = R_{LB} - (R_{LB}^2 - Y_{P2}^2)^{\frac{1}{2}}$$

Next, a point on the anterior surface of the conformed ICL is defined $(X_{A2}, Y_{A2})$ such that:

$$Y_{A2} = Y_{P2}$$

and $$X_{A2} = X_{P2} + t_A(Y_{P2}) \quad (2)$$

where $t_A (Y_{P2})$ is the thickness parallel to the axis of the conformed ICL as a function of $Y_{P2}$. The function of $t_A(Y_{P2})$ is to be determined.

The line segment, $t_A$, which will be horizontal in the conformed state, is initially at angle $\alpha$ from the horizontal. Assuming conservation of angles in the transformation, the line segment, $t_A$, will be rotated by the same angle that a line perpendicular to the surface rotates. A radius, such as $R_{BC}$ rotates by $\theta_2 - \theta_1$. Since conservation of radial arc length along the BC has been assumed, $$R_{BC}\theta_1 = R_{LB}\theta_2.$$

So, $$\alpha = \theta_2 - \theta_1.$$

becomes $$\alpha = \left(\left(\frac{R_{BC}}{R_{LB}}\right) - 1\right)\theta_1$$

or $$\alpha = \left(\left(\frac{R_{BC}}{R_{LB}}\right) - 1\right)\arcsin\left(\frac{Y_{P1}}{R_{BC}}\right)$$

Taking as a coordinate system in the relaxed state $(X_1, Y_1)$ with the origin at the vertex of the anterior ICL surface, the line containing $t_A$ which passes through $(X_{P1}, Y_{P1})$ is:

$$Y_1 M X_1 + B \quad (3)$$

$M = \tan(\alpha)$
$B = Y_{P1} M(X_{P1} + t_{ICL})$ and $t_{ICL}$ = the ICL center thickness
The equation of the anterior surface is:

$$R^2_{AL} = (X_1 - R_{AL})^2 + Y_1^2 \quad (4)$$

where $R_{AL}$ = the relaxed ICL anterior radius of curvature (ROC)

The intersection $(X_{A1}, Y_{A1})$ can be found by solving equations (3) & (4), $$X_{A1} = \frac{(R_{AL} - MB) - (R_{AL}^2 - 2R_{AL}MB - B^2)^{\frac{1}{2}}}{(1 + M^2)} \quad (5)$$

and $Y_{A1} = X_{A1} M + B.$

Thus, the parallel thickness $t_A$ in the conformed state will be $$t_A(Y_{P2}) = ((X_{A1} - X_{P1})^2 + (Y_{A1} - Y_{P1})^2)^{\frac{1}{2}} \quad (6)$$

and the coordinates of the conformed ICL anterior can be found using the equations (2).

The geometric ray tracing takes twenty points along one half of the optic zone and approximates rays normal to the surface with perpendicular bisectors between adjacent pairs of points. The intersections of these rays are determined and the lengths averaged to obtain the best fit sphere's ROC. The deviation from sphericity is determined by tabulating the differences between the average ROC and the lengths from the surface to the intersections of each pair of adjacent rays across the optical zone. The measure of deviation from sphericity is taken as the slope of the local deviation with respect to optic zone radius at the point where the local curvature matches the average (see FIG. 6).

These calculations were performed for ICLs of power in the range $-1.0$ to $-30.0$ diopters, with a base curve of 7.549 mm radius of curvature designed for a 43 diopter cornea mismatched onto corneas with a power in the range 38-51 diopters. Table 3 shows expected change in ICL power due to the mismatch, and demonstrates the the information can be used to select the ICL power for a given corneal power to obtain the desired prescribed refraction. In conclusion, the actual power of the lens due to any mismatch is either clinically insufficient or can be compensated for by selecting a power which adjusts for the projected mismatch.

TABLE 3

Variation in Correction Predicted Due to Curvature Mismatch Between Patient Corneal Bed and Intracorneal Lens Posterior Surface Corresponding to a 43 Diopter Cornea Minus 0.3 mm Lamellar Section

| Preoperative Corneal Power as Determined by a Keratometer | | | | | |
|---|---|---|---|---|---|
| 38.00 | −4.94 | −10.00 | −15.05 | −20.10 | −25.16 | −30.21 |
| 38.50 | −4.95 | −10.00 | −15.04 | −20.09 | −25.14 | −30.19 |
| 39.00 | −4.95 | −10.00 | −15.05 | −20.08 | −25.12 | −30.16 |
| 39.50 | −4.96 | −10.00 | −15.04 | −20.07 | −25.11 | −30.14 |
| 40.00 | −4.96 | −10.00 | −15.03 | −20.06 | −25.09 | −30.12 |
| 40.50 | −4.97 | −10.00 | −15.02 | −20.06 | −25.07 | −30.10 |
| 41.00 | −4.98 | −10.00 | −15.02 | −20.04 | −25.06 | −30.08 |
| 41.50 | −4.98 | −10.00 | −15.01 | −20.03 | −25.04 | −30.06 |
| 42.00 | −4.99 | −10.00 | −15.01 | −20.02 | −25.06 | −30.04 |
| 42.50 | −4.99 | −10.00 | −15.00 | −20.01 | −25.03 | −30.02 |
| 43.00 | −5.00 | −10.00 | −15.00 | −20.00 | −25.00 | −30.00 |
| 43.50 | −5.01 | −10.00 | −14.99 | −19.99 | −24.98 | −29.97 |
| 44.00 | −5.01 | −10.00 | −14.99 | −19.98 | −24.96 | −29.95 |
| 44.50 | −5.02 | −10.00 | −14.98 | −19.97 | −24.95 | −29.93 |
| 45.00 | −5.03 | −10.00 | −14.98 | −19.96 | −24.93 | −29.91 |
| 45.50 | −5.03 | −10.00 | −14.97 | −19.95 | −24.92 | −29.89 |
| 46.00 | −5.04 | −10.01 | −14.97 | −19.94 | −24.91 | −29.87 |
| 46.50 | −5.05 | −10.01 | −14.97 | −19.93 | −24.89 | −29.85 |
| 47.00 | −5.05 | −10.01 | −14.96 | −19.92 | −24.88 | −29.83 |
| 47.50 | −5.06 | −10.01 | −14.96 | −19.91 | −24.86 | −29.81 |
| 48.00 | −5.07 | −10.01 | −14.96 | −19.90 | −24.85 | −29.79 |
| 48.50 | −5.08 | −10.02 | −14.95 | −19.89 | −24.83 | −29.77 |
| 49.00 | −5.08 | −10.02 | −14.95 | −19.88 | −24.82 | −29.75 |
| 49.50 | −5.09 | −10.02 | −14.95 | −19.88 | −24.80 | −29.73 |

TABLE 3-continued

Variation in Correction Predicted Due to Curvature
Mismatch Between Patient Corneal Bed and Intracorneal
Lens Posterior Surface Corresponding to a 43 Diopter
Cornea Minus 0.3 mm Lamellar Section Preoperative
Corneal Power
as Determined
by a Keratometer

| 50.00 | −5.10 | −10.02 | −14.94 | −19.87 | −24.79 | −29.72 |

Referring to Table 3, it is believed that accurate predictions of actual power due to mismatch demonstrate that the mismatch can be compensated for. Therefore, the scientific assumptions used as a basis for the intracorneal lens I of this invention, including the utilization of a constant base posterior curvature, are valid for patients having preoperative keratometer readings in the range of 38–51 diopters.

The clinician can determine the desired corneal correction as follows. When possible, the patient is refracted using a phoropter. The spherical equivalent of the manifest refraction should be converted to the corneal plane using the vertex distance. This conversion can be done with the tables in the Physician's Desk Reference for Ophthalmology. For example, if the patient's refraction is: $-11.00 - 1.00 \times 90°$, then the spherical equivalent is: $-11.50$ diopters. If the vertex distance is 13 mm, then the required corneal correction is: $-10.00$ diopters. Once the refracted correction for achieving emmetropia is determined, the clinician may select a different refracted correction than that on account of other factors such as actual lamellar bed radius, patient environment or activity factors and the like.

The clinician can also adjust the actual power selected to account for the power shift due to the inner corneal lens base curve mismatch. This power shift will be predictable utilizing the information set forth in the foregoing test with the development of appropriate tables based upon this information.

The foregoing disclosure and description of the invention are illustrative and explanatory thereof, and various changes in the size, shape and materials, as well as in the details of the illustrated construction may be made without departing from the spirit of the invention.

We claim:

1. A biocompatible lens for implantation into a cornea of the human eye for correction of myopia wherein a cornea cap section is removed and a corneal implant bed is created, comprising:
   a) a one-piece body having a central axis, a peripheral edge, an anterior surface and a posterior surface, the body being generally circular with respect to the central axis, the anterior surface being generally convex and the posterior surface being generally concave with respect to a plane normal to the central axis;
   b) a peripheral transition zone joining the anterior surface to the posterior surface having an annular surface with a planar surface that is parallel to a plane normal to the central axis, the planar surface joining the posterior surface to extend radially outwardly therefrom for allowing the lens to be implanted onto the corneal bed and for allowing a smooth overlay of the corneal cap section so that a postoperative corneal anterior surface radius of curvature is increased;
   c) a posterior surface central curve radius of between approximately 6.318 and 8.582 millimeters;
   d) an anterior surface central curve radius of between approximately 7.766 and 11.162 millimeters;
   e) a thickness between the anterior surface and the posterior surface at the central axis that is less than at the peripheral transition zone and generally falling within the range of 0.05 to 0.20 millimeters;
   f) a body diameter of between approximately 5.0 and 8.0 millimeters; and
   g) an implanted refractive power substantially less than a resultant alteration in a refractive power of an anterior surface of the cornea.

2. The lens of claim 1 further comprising a toric surface on the anterior surface of the lens for the correction of myopia with accompanying astigmatism by altering the refractive power of the anterior surface of the cornea.

3. The lens of claim 1 further comprising a toric surface on the posterior surface of the lens for the correction of myopia with accompanying astigmatism by altering the refractive power of the anterior surface of the cornea.

4. The lens of claim 1 wherein the peripheral transition zone further comprising a second annular surface that cooperates with the first-mentioned annular surface to join the anterior surface and the posterior surface.

5. The lens of claim 4 wherein the peripheral transition zone further comprising a third annular surface that cooperates with the second and the first-mentioned annular surfaces to join the anterior surface and the posterior surface.

6. The lens of claim 5 wherein a width of the third annular surface is constant regardless of the anterior surface central curve radius.

7. The lens of claim 5 wherein a width of the third annular surface varies proportionally to the anterior surface central curve radius.

8. The lens of claim 1 wherein the annular surface further comprises a cylindrical surface adjoining the planar surface having an axis coterminous with the central axis of the lens and forming the peripheral edge.

9. The lens of claim 8 wherein the annular surface further comprises a spherical surface having an axis coterminous with the central axis of the lens and extending from a first junction with the cylindrical surface radially inward into a second junction with the anterior surface.

10. The lens of claim 9 wherein the spherical surface has a spherical radius of curvature that is less than the posterior surface central curve radius and the anterior surface central curve radius.

11. The lens of claim 9 wherein the thickness is less at the central axis than at the second junction.

12. The lens of claim 1 wherein the posterior surface central curve radius is approximately 7.548 millimeters.

13. The lens of claim 1 wherein the body diameter is approximately 6.00 millimeters.

14. The lens of claim 1 wherein the body diameter is approximately 6.75 millimeters.

15. The lens of claim 1 wherein the thickness is approximately 0.100 millimeters.

16. The lens of claim 1 wherein the body comprises hydrogel.

17. A biocompatible lens for implantation into the cornea of the human eye for correction of myopia wherein a cornea cap section is removed and a corneal implant bed is created, comprising:

a) a one-piece body having a central axis, a peripheral edge, an anterior surface and a posterior surface, the body being generally circular with respect to the central axis, the anterior surface being generally convex and the posterior surface being generally concave, both with respect to a plane normal to the central axis;

b) a peripheral transition zone joining the anterior surface to the posterior surface having a first annular surface and a cooperating second annular surface for allowing the lens to be implanted onto the corneal bed and for allowing a smooth overlay of the corneal cap section so that a postoperative corneal anterior surface radius of curvature is increased;

c) a thickness between the anterior surface and the posterior surface at the central axis that is less than at the peripheral transition zone; and d) an implanted refractive power substantially less than a resultant alteration in a refractive power of an anterior surface of the cornea.

18. The lens of claim 17 wherein the peripheral transition zone further comprising a third annular surface that cooperates with the second and the first annular surfaces to join the anterior surface and the posterior surface.

19. The lens of claim 18 wherein a width of the third annular surface is constant regardless of the anterior surface central curve radius.

20. The lens of claim 18 wherein a width of the third annular surface varies proportionally to the anterior surface central curve radius.

21. The lens of claim 17 wherein the first annular surface comprises a planar surface that is parallel to a plane normal to the central axis, the planar surface joining the posterior surface to extend radially outwardly therefrom.

22. The lens of claim 21 wherein the second annular surface comprises a cylindrical surface adjoining the planar surface having an axis coterminous with the central axis of the lens and forming the peripheral edge.

23. The lens of claim 22 wherein the annular surface further comprises a spherical surface having an axis coterminous with the central axis of the lens and extending from a first junction with the cylindrical surface radially inward into a second junction with the anterior surface.

24. The lens of claim 23 wherein the spherical surface has a spherical radius of curvature that is less than both the posterior surface central curve radius and the anterior surface central curve radius.

25. The lens of claim 17 further comprising a toric surface on the anterior surface of the lens for the correction of myopia with accompanying astigmatism by altering the refractive power of the anterior surface of the cornea.

26. The lens of claim 17 further comprising a toric surface on the posterior surface of the lens for the correction of myopia with accompanying astigmatism by altering the refractive power of the anterior surface of the cornea.

27. A hydrogel lens for implantation into the cornea of the human eye for correction of myopia wherein a cornea cap section is removed and a corneal implant bed is created, comprising:

a) a one-piece body having a central axis, a peripheral edge, an anterior surface and a posterior surface, the body being generally circular with respect to the central axis, the anterior surface being generally convex and having a central curve radius of between approximately 7.766 and 11.162 millimeters and the posterior surface being generally concave with respect to a plane normal to the central axis and having a central curve radius of approximately 7.549 millimeters;

b) a peripheral transition zone joining the anterior surface to the posterior surface for allowing the lens to be implanted onto the corneal bed and for allowing a smooth overlay of the corneal cap section so that a postoperative corneal anterior surface radius of curvature is increased, having
   i) a planar surface that is parallel to a plane normal to the central axis, the planar surface joining the posterior surface to extend radially outwardly therefrom,
   ii) a cylindrical surface adjoining the planar surface having an axis coterminous with the central axis of the lens and forming the peripheral edge and
   iii) a spherical surface having an axis coterminous with the central axis of the lens and extending from a first junction with the cylindrical surface radially inward into a second junction with the anterior surface;

c) a thickness between the anterior surface and the posterior surface at the central axis that is less than at the peripheral transition zone and approximately 0.100 millimeters;

d) a body diameter of between approximately 6.0 and 6.75 millimeters; and e) an implanted refractive power substantially less than a resultant alteration in a refractive power of an anterior surface of the cornea.

28. The lens of claim 27 further comprising a toric surface on the anterior surface of the lens for the correction of myopia with accompanying astigmatism by altering the refractive power of the anterior surface of the cornea.

29. The lens of claim 27 further comprising a toric surface on the posterior surface of the lens for the correction of myopia with accompanying astigmatism by altering the refractive power of the anterior surface of the cornea.

* * * * *

UNITED STATES PATENT AND TRADEMARK OFFICE
CERTIFICATE OF CORRECTION

PATENT NO. : 5,123,921                      Page 1 of 2
DATED : June 23, 1992
INVENTOR(S) : Werblin, Patel It is certified that error appears in the above-indentified patent and that said Letters Patent is hereby corrected as shown below:

On the title page, the title of the invention should read --Synthetic Intracorneal Lens and Method of Manufacture-- c.1, 1.2, delete "LINES" substitute therefore --LENS-- c.2, 1.45, delete "to Cal-" substitute therefore --to cal--- c.3, 1.40, delete "Join" substitute therefore --join-- c.5, 1.5, delete "Join" substitute therefore --join--

UNITED STATES PATENT AND TRADEMARK OFFICE
CERTIFICATE OF CORRECTION

PATENT NO. : 5,123,921

DATED : June 23, 1992

INVENTOR(S) : Werblin, Patel

It is certified that error appears in the above-identified patent and that said Letters Patent is hereby corrected as shown below:

c.6, 1.46, delete "Whereever" substitute --Wherever-- c.10, 1.43, delete "intraocular" substitute therefore --intracorneal-- c.10, 1.47, delete "intraocular" substitute therefore --intracorneal-- c.12, 1.35, delete "strates the the" substitute therefore --strates thec.14, 1.25, delete "comprising" substitute therefore --comprises-- c.14, 1.29, delete "comprising" substitute therefore --comprises-- c.15, 1.23, delete "comprising" substitute therefore --comprises--

Signed and Sealed this

Twenty-sixth Day of October, 1993

*Attest:*

BRUCE LEHMAN

*Attesting Officer*   Commissioner of Patents and Trademarks